(12) United States Patent
Lewalter et al.

(10) Patent No.: US 7,782,999 B2
(45) Date of Patent: Aug. 24, 2010

(54) SYSTEMS AND METHODS FOR SCANNING AND DATA ACQUISITION IN COMPUTED TOMOGRAPHY (CT) APPLICATIONS

(75) Inventors: Astrid Lewalter, Aachen (DE); Rainer Pietig, Herzogenrath (DE); Guenter Zeitler, Aachen (DE); Kai Eck, Aachen (DE); Christoph Herrmann, Aachen (DE); Rainer Kiewitt, Roetgen (DE); Christoph Loef, Aachen (DE); Oliver Muelhens, Aachen (DE); Carolina Ribbing, Aachen (DE); Georg Rose, Duesseldorf (DE); Matthias Simon, Aachen (DE); Olaf Wischhusen, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 16 days.

(21) Appl. No.: 12/096,443

(22) PCT Filed: Sep. 16, 2006

(86) PCT No.: PCT/IB2006/053331
§ 371 (c)(1),
(2), (4) Date: Oct. 28, 2008

(87) PCT Pub. No.: WO2007/066243
PCT Pub. Date: Jun. 14, 2007

(65) Prior Publication Data
US 2009/0161819 A1    Jun. 25, 2009

Related U.S. Application Data

(60) Provisional application No. 60/748,672, filed on Dec. 8, 2005.

(51) Int. Cl.
*H05G 1/60* (2006.01)
*H01J 35/30* (2006.01)

(52) U.S. Cl. .......................................... 378/16; 378/136
(58) Field of Classification Search ...................... 378/4, 378/15, 16, 19, 136
See application file for complete search history.

(56) References Cited

U.S. PATENT DOCUMENTS 3,852,605 A    12/1974    Watanabe et al.

(Continued)

FOREIGN PATENT DOCUMENTS

WO    2004061864 A2    7/2004

*Primary Examiner*—Irakli Kiknadze

(57) ABSTRACT

Systems and methods for data acquisition in computed tomography (CT) applications are provided. The systems and methods are particularly adapted for scanning and acquiring/processing data in connection with high-power cone-beam CT applications. The electron beam is moved/scanned along the anode surface to multiple focal positions. Data acquisition for a full projection at one focus position and one view angle is achieved by activating each focus position multiple times during the data acquisition for one angle of the gantry. The detector array and associated data processing system are adapted to rapidly switch between the different focus positions during the acquisitions for one view angle and to collect all data belonging to the same projection into the same data set. Adaptive electron optics are utilized to move/scan the electron beam along the anode surface to the various focus positions. Alternatively, a plurality of cathodes may be provided for respective focus positions and the system may support fast switching therebetween to achieve desirably short spot times. The disclosed CT system permits greater power densities without risk of heat damage to the anode and effectively increases the track velocity of the electron beam on the anode surface. The CT system and associated data acquisition methods have particular utility in CT applications requiring increased time resolution and/or spatial resolution, e.g., cardiac CT applications.

23 Claims, 3 Drawing Sheets

U.S. PATENT DOCUMENTS

| | | |
|---|---|---|
| 4,637,040 A | 1/1987 | Sohval et al. |
| 6,256,369 B1 | 7/2001 | Lai |
| 6,879,655 B2 | 4/2005 | Proksa |
| 6,894,281 B2 | 5/2005 | Such et al. |
| 6,904,117 B2 | 6/2005 | Hein et al. |
| 6,907,099 B2 | 6/2005 | Kling et al. |
| 6,917,664 B2 | 7/2005 | Chappo et al. |
| 2005/0053189 A1 | 3/2005 | Gohno et al. |
| 2005/0094762 A1 | 5/2005 | Dunham et al. |
| 2005/0147201 A1 | 7/2005 | Hoffman |
| 2005/0152491 A1 | 7/2005 | Francke et al. |

SYSTEMS AND METHODS FOR SCANNING AND DATA ACQUISITION IN COMPUTED TOMOGRAPHY (CT) APPLICATIONS

CROSS REFERENCE TO RELATED APPLICATIONS

This application claims the benefit of U.S. provisional application Ser. No. 60/748,672 filed Dec. 8, 2005, which is incorporated herein by reference.

The present disclosure is directed to systems and methods for data acquisition in computed tomography (CT) applications and, more particularly, to systems and methods for scanning and acquiring/processing data in connection with high-power cone-beam CT applications.

Computed tomography (CT) systems use x-rays to produce detailed images/pictures of internal anatomical structures. Generally, a CT system directs x-rays through the body in a continuous manner, i.e., a continuous x-ray beam is directed to the patient. Thereafter, the detected photons are clustered into views or frames via successive detector readouts. Each "view" or a "frame" represents a projection picture of the organ or area being studied. The frames or views are collected and these data are used to reconstruct 2D images ("slices") or even 3D images of the organ or area being studied. Dense tissue, such as bone, appear white on a typical CT image while less dense tissue, e.g., brain tissue or muscle, generally appear in shades of gray. Air-filled spaces, e.g., in the bowel or lung, appear black. CT scans can be used to obtain information about a wide variety of anatomical structures, e.g., the liver, pancreas, intestines, kidneys, adrenal glands, lungs, and heart, blood vessels, the abdominal cavity, bones, and the spinal cord.

CT imaging typically employs an x-ray source that generates a fan-beam or cone-beam of x-rays that traverse an examination region. A subject positioned in the examination region interacts with and absorbs a portion of the traversing x-rays. Standard x-ray sources include a single cathode that emits an electron beam, which is accelerated and focused onto a single focus on an anode. Upon collision with the anode, a small fraction of the incident electron energy is converted into x-rays. A large percentage of the incident energy is translated to heat and deposited in the anode. To prevent anode damage due to the incident heat, the anode typically takes the form of a rotating disk, thereby defining a relative velocity between the incident electron beam and the anode surface (referred to as the "track velocity"). Generally, the higher the track velocity associated with a CT system, the higher the power density that can be obtained from the CT system. Although the track velocity can be increased by increasing the radius of the anode disk and/or by increasing its rotation speed/frequency, the technical limits for such approaches to increasing power density have been approached, if not reached.

A CT data measurement system (DMS) generally includes a two-dimensional detector array arranged opposite the x-ray source to detect and measure intensities of the transmitted x-rays. Typically, the x-ray source and the DMS are mounted at opposite sides of a rotating gantry. As the gantry is rotated, an angular range of projection views of the subject are obtained.

The two-dimensional detector array of the DMS typically includes a scintillator crystal or array of scintillators which produce bursts of light, called scintillation events, responsive to impingement of x-rays onto the scintillator. A two-dimensional array of photodetectors, such as photodiodes or photomultiplier tubes, are arranged to view the scintillator and produce analog electrical signals in response to the scintillation events. The analog electrical signals are routed via electrical connections to an analog-to-digital converter which digitizes the analog signals. The digitized signals are multiplexed into a reduced number of transmission channels, and the transmission channels communicate the multiplexed digitized signals.

Increasingly, CT systems utilize multi-slice cone-beam detectors to obtain three dimensional (3D) projection datasets of a subject, e.g., a patient. CT systems that employ such multi-slice cone-beam detectors are generally effective for reconstruction of an entire scanned volume. In helical CT imaging, the patient is advanced linearly through the examination region along a direction that is perpendicular to the gantry rotation plane to effectuate a helical orbiting of the x-ray source about the subject. X-ray absorption data obtained during the helical orbiting is reconstructed, e.g., using filtered back-projection or another reconstruction method, to generate 3D image representation of the subject (or selected portion(s) thereof).

The patent literature discloses CT systems for use in image capture/generation. Exemplary patents and patent publications of potential background relevance to the present disclosure are U.S. Pat. No. 6,879,655 to Proksa ("Computed Tomography Apparatus"), U.S. Pat. No. 6,894,281 to Such et al. ("Grid for the Absorption of X-Rays"), U.S. Pat. No. 6,904,117 to Hein et al. ("Tilted Gantry Helical Cone-Beam Feldkamp Reconstruction for Multislice CT"), U.S. Pat. No. 6,907,099 to Kling et al. ("Method and Apparatus for Computed Tomography Imaging"), U.S. Pat. No. 6,917,664 to Chappo et al. (Symmetrical Multiple-Slice Computed Tomography Data Management System"), and U.S. Patent Publication No. 2005/0094762 to Dunham et al. ("Method and Apparatus for Z-Axis Tracking and Collimation"). In addition, in the field of tomosynthesis, U.S. Patent Publication No. 2005/0152491 to Francke et al. ("Scanning-Based Detection of Ionizing Radiation for Tomosynthesis") is of potential background relevance.

Despite efforts to date, a need remains for CT systems and methods that can deliver higher time resolution (in order to obtain high quality images from moving objects, e.g., the heart) and/or higher spatial resolution (e.g., for improved imaging of small structures/details, e.g., blood vessel properties). In addition, a need remains for CT systems and methods that can deliver higher peak x-ray power from an x-ray source. Further, a need remains for CT systems and methods that can overcome the potential over-heating of x-ray tube(s) at or near the focal spot on the anode, particularly when the peak power density is increased in connection with scan(s) using a multi-slice cone-beam CT system. These and other needs are met by the CT systems and methods described herein.

According to the present disclosure, computed tomography (CT) systems and methods are provided that are adapted to deliver higher time resolution and/or higher spatial resolution, thereby enabling high quality images from moving objects and improved imaging of small structures and/or structural details. The disclosed CT systems and methods deliver higher peak x-ray power from an x-ray source, while simultaneously overcoming the potential for over-heating of x-ray tube(s) at or near the focal spot on the anode. Thus, the disclosed CT systems and methods are adapted to operate reliably and effectively as peak power density is increased, e.g., in connection with scan(s) using a multi-slice cone-beam CT system.

According to exemplary embodiments of the present disclosure, a CT system is provided that includes an x-ray tube for directing an x-ray beam toward a structure, e.g., a patient, and a detector array positioned opposite the x-ray tube. The x-ray tube and detector array are generally mounted on a gantry that is adapted to rotate relative to a subject positioned therewithin. A control mechanism and associated control circuitry are typically provided for controlling operation of the CT system, e.g., rotation of the gantry, image capture and the like. Analog electrical signals are generated by the detector array and routed to an analog-to-digital converter which digitizes the analog signals. Thus, as the gantry is rotated, an angular range of projection views of the subject are obtained.

Enhanced data acquisition is achieved according to the present disclosure through a rapid, high-power computed tomography (CT) system. The advantageous CT system of the present disclosure includes an x-ray tube that allows/facilitates rapid motion of its focus along the patient axis. In an exemplary embodiment of the present disclosure, fast successive switching may be employed between the various focus positions along the patient axis, e.g., by providing a separate cathode for each focus position and performing fast switching between the cathodes. This fast successive switching technique can also be viewed as establishing a high effective spot velocity. Furthermore, in the present disclosure, a CT system is provided that combines gantry rotation with axial motion of x-ray focus along the patient axis to provide a full projection of the patient for each focus position. Moreover, the disclosed CT system generates a full projection of the patient at each view angle of the gantry. Exemplary embodiments of the present disclosure include a multi-slice cone-beam detector assembly that is adapted for rapid data acquisition/processing, such that data acquisition associated with multiple focus positions along the patient axis is effectively correlated to yield full projections, as described herein.

The disclosed data acquisition methodology collects/processes detector readings by activating each focus position multiple times for each view angle associated with gantry operation. Thus, unlike prior art data acquisition techniques that obtain view angle readings in a sequential fashion—only collecting data for a given view angle in a single activation—the CT system of the present disclosure is advantageously adapted for repeated activation at a given view angle. The detector assembly and data processing system are adapted to correlate the then-addressed focus position with a specific data set, and to collect/combine all data for such focus position and such view angle into the same data set, as the CT system repeatedly activates readings at such focus position for the same view angle. In this way, sufficient data for generation of full projections is generated for each focus position.

The disclosed CT system and associated data acquisition methodology are particularly advantageous in that the photons required for a given projection can be produced in several different time slots, i.e., based on the repeated activation for a given view angle. As a result, the track velocity of the electron beam on the anode of the x-ray tube may be increased, thereby allowing the x-ray tube to be operated at higher peak power density without the attendant risks to the anode and overall x-ray tube operation. Thus, unlike conventional CT systems that generate the requisite photons for each view angle in a single block of time, the disclosed CT system segregates/divides such photon generation into multiple time slots.

Since the disclosed CT systems and data acquisition methods allow operating the x-ray source at a higher peak power density, the advantageous system designs of the present disclosure can be used to deliver higher time resolution (facilitating high quality images for moving objects, e.g., the heart) and/or higher spatial resolution (facilitating imaging of small structures/details, e.g., blood vessel properties). Additional advantageous features and functions of the disclosed CT systems and associated data acquisition methods will be apparent from the detailed description which follows.

To assist those of ordinary skill in the art in making and using the disclosed CT systems, reference is made to the accompanying figures, wherein.

The present disclosure provides computed tomography (CT) systems and data acquisition/processing methods that are adapted to deliver higher time resolution and/or higher spatial resolution, thereby enabling high quality images from moving objects and improved imaging of small structures and/or structural details. Exemplary embodiments of the present disclosure deliver higher peak x-ray power from an x-ray source and overcome the potential for over-heating of x-ray tube(s) at or near the focal spot on the anode.

Figure 1:
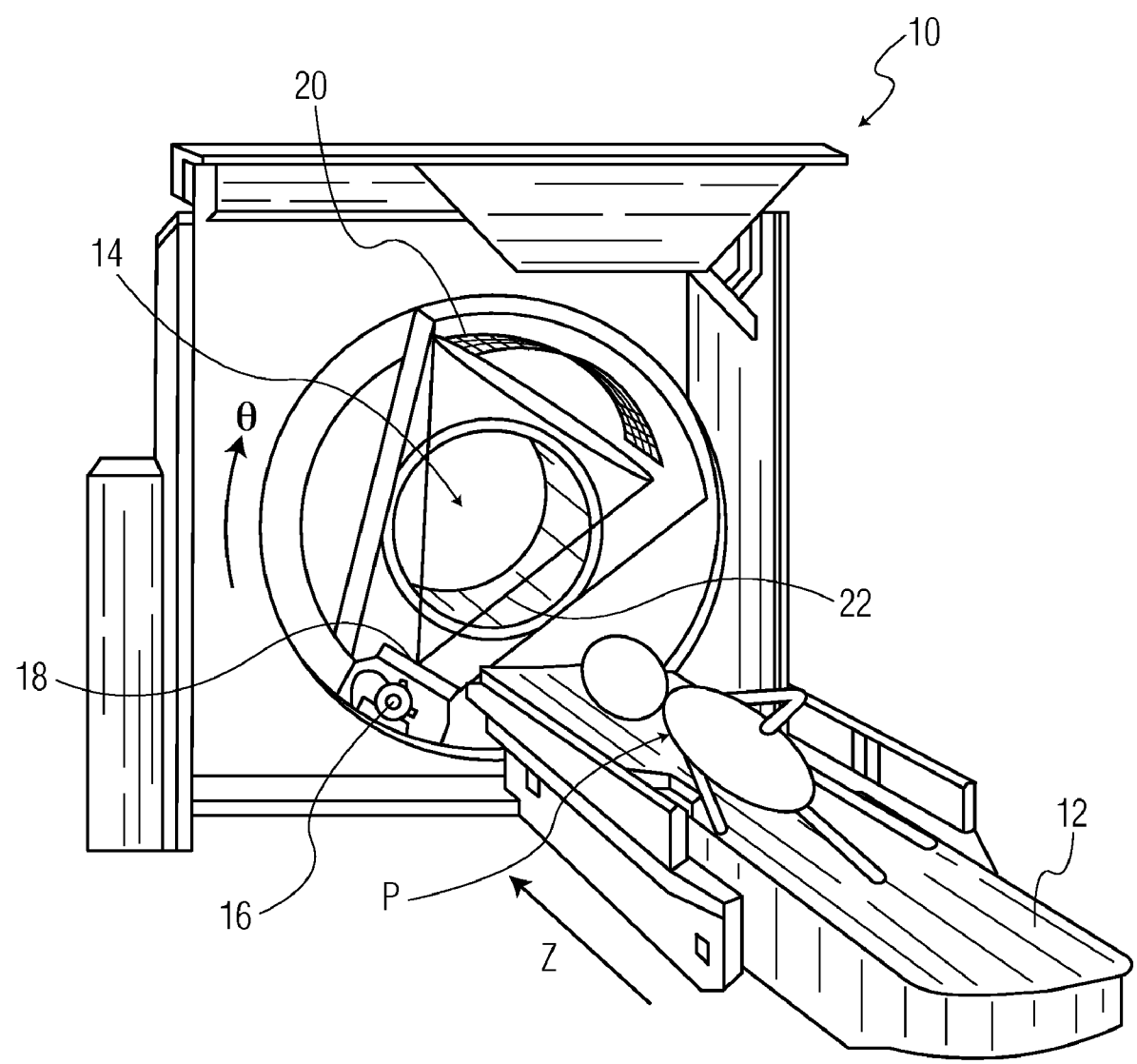
FIG. 1 is a schematic diagram of a computed tomography system according to the present disclosure.

With initial reference to FIG. 1, an exemplary CT system 10 is schematically depicted. CT system 10 includes an imaging subject support 12, such as a couch, which is linearly/axially movable along a Z-axis inside an examination region 14. An x-ray tube assembly 16 is mounted on a rotating gantry and is adapted to project x-rays through the examination region 14. A collimator 18 (e.g., an adjustable collimator) collimates the radiation in two dimensions. Normally, a fan beam or a cone beam is collimated out. With prior art systems, this x-ray tube assembly usually provides one anode and one cathode and a basically fixed focus position with respect to the collimator. However, the disclosed systems and techniques provide enhanced performance relative to such prior art designs, as described in greater detail below.

An x-ray detector array 20 is disposed on the rotating gantry across the examination region 14 from the x-ray tube assembly 16. In an alternative embodiment of the present disclosure, the x-ray detector array may take the form of non-rotating two-dimensional detector rings, e.g., detector rings that are mounted on a stationary gantry positioned around the rotating gantry. Detector array 20 generally includes a plurality of parallel detector rows of detector elements, such that projection data corresponding to a plurality of quasi-parallel or parallel slices can be acquired simultaneously during a scan.

The x-ray source generally projects a cone-shaped beam, which is collimated in such a way that it has a fan shape with a certain opening angle ("fan angle") that lies in an X-Y plane of a Cartesian coordinate system (generally referred to as an "imaging plane") and another finite aperture in the direction orthogonal to this imaging plane with another certain opening angle (generally referred to as a "cone angle"). The x-ray beam passes through an object being imaged, such as a patient. The beam, after being attenuated by the object, impinges upon an array of radiation detector elements. The intensity of the attenuated radiation beam received at the detector array is dependent upon the attenuation of an x-ray beam by the object. Each detector element of the array produces a separate electrical signal that is a measurement of the detected x-ray photons (this is, of the beam intensity) at the detector location. The intensity measurements from all the detector elements are acquired separately to produce a transmission profile. A group of x-ray attenuation measurements, i.e., projection data, from the detector array at one gantry angle is referred to as a "view".

A control mechanism and associated control circuitry (not pictured) are typically provided for controlling operation of CT system 10, e.g., rotation of the gantry, image capture and the like. Analog electrical signals are generated by the detector array 20 and routed to an analog-to-digital converter which digitizes the analog signals. Thus, as the gantry is rotated, an angular range of projection views of the subject are obtained.

The control mechanism associated with the disclosed CT system 10 generally includes an x-ray controller that provides power and timing signals to x-ray source 14 and a gantry motor controller that controls the rotational speed and position of components on gantry. A data acquisition system (DAS) in the control mechanism samples analog data from detector elements 20 and converts the data to digital signals for subsequent processing. An image reconstructor receives sampled and digitized x-ray data from the DAS and performs high-speed image reconstruction. The reconstructed image is generally applied as an input to a computer, which stores the image in a storage device. The image reconstructor can take the form of specialized hardware and/or computer programs executing on the computer.

The computer is also generally adapted to receive commands and scanning parameters from an operator via a console that has a keyboard. An associated display allows the operator to observe the reconstructed image and other data from the computer. The operator-supplied commands and parameters are used by the computer to provide control signals and information to the DAS, x-ray controller, and/or gantry motor controller. In addition, the computer generally operates a table motor controller, which controls the imaging subject support 12 to position the patient "P" in the gantry.

According to the present disclosure, enhanced data acquisition is achieved by adapting the x-ray tube to rapidly move its focus along the patient axis over distances large compared to the optical length of the focus. The disclosed CT system combines gantry rotation with axial motion of x-ray focus along the patient axis to provide a full projection of the patient for each focus position, thereby generating a full projection of the patient at each view angle of the gantry. In an exemplary embodiment of the present disclosure, both the x-ray source and detector array are mounted on a rotating gantry in such a way that, for all angular positions of the gantry, every focus position of the x-ray source can exactly illuminate the entire detector area. The DAS associated with the disclosed CT system collects and processes readings from the detector array by activating each focus position multiple times for each view angle associated with gantry operation. The detector array is generally provided with or in communication with a means to allow readings of all its elements in very short succession. An exemplary means for making such readings is a photon counting detector array. The DAS further correlates each reading of each detector element with the respective position of the focus and the respective view angle at the time of the measurement, and combines all data for a same focus position and a same view angle into the same data set, as the CT system repeatedly activates readings at such focus position and such view angle. In this way, sufficient data for generation of full projections is generated for each focus position at each view angle.

In an exemplary embodiment of the present disclosure, the CT system includes an x-ray tube having an elongated cylindrical rotating anode that extends along the patient axis, i.e., the Z-axis, of the CT system. Alternative anode designs may be employed, e.g., an elongated helical anode and/or a saddle anode or a collection of several distinct anodes along the z-axis. In implementations wherein multiple anodes are incorporated into a CT system, such plurality of anodes may be referred to as an "anode system". The anode or anode system cooperates with a single cathode or multiple cathodes that is/are adapted to direct an electron beam thereagainst. In implementations wherein multiple cathodes are employed, such plurality of cathodes may be referred to as a "cathode system".

According to an exemplary embodiment of the present disclosure, adaptive electronic optics are positioned between the cathode/cathode system and the anode/anode system so as to scan the electron beam along the anode in a focused manner, thereby continually moving the electron beam focus along the z-axis of the anode/anode system. Electronic optics for redirecting/controlling the flow of electrons in an electronic beam are well known, and such known electronic optics systems/designs are expressly incorporated herein by reference. Operation of the adaptive electronic optics is generally controlled by the controller associated with the disclosed CT system and is effective to effect a very fast motion of the electron beam along the z-axis. The electron beam movement along the z-axis may be performed in a substantially continuous motion or in a motion characterized by a series of discrete steps along the z-axis.

In an alternative implementation of the present disclosure, a plurality of conventional anode disks or other anode elements may be positioned in a substantially side-by-side orientation along the patient axis, i.e., the z-axis of the CT system. The anode array may be adapted to cooperate with a single cathode or multiple cathodes positioned along the Z-axis of the CT system. In either case, adaptive electronic optics are advantageously positioned between the cathode(s) and the anode elements so as to effect a continuous or stepwise motion of the focus of each electron beam. In this way, the electron beam is rapidly and continually relocated on the surface of the anode element(s), thereby minimizing the potential for over-heating and other deleterious effects on the anode array.

The detector array associated with the disclosed CT system is adapted to receive x-ray beams from the x-ray source. The detector array generally functions as a multi-slice cone-beam detector that, in combination with the disclosed DAS, is advantageously adapted for rapid switching of the readout between different acquisition slots, e.g., switching at a frequency of 1 MHz and possibly even more rapidly. Alternatively, the disclosed detector array and associated DAS may be adapted to detect and count photons at low levels, e.g., individual photons, and save/retain this photon data together with the precise acquisition time, such that received photons for a given projection can be effectively combined into one data set once the multiple readings have been obtained.

The disclosed methodology for rapidly repositioning the focus of the electron beam (or electron beams) on the anode surface (or anode surfaces) enhances the power density capabilities of the disclosed CT system. Moreover, the increased power densities supported by the disclosed CT system translate to a dramatically reduced time requirement for collection of the requisite photons for a single projection, e.g., a time reduction of about half for a doubled power density.

From a quantitative standpoint, the temperature increase at the focal spot on the anode surface may be calculated using the following relationship:

$$\Delta T = kP \cdot \sqrt{\Delta t}$$

with "T" being the temperature, "P" being the power density, k being a constant, and "Δt" being the time that the electron beam is heating a certain spot, also called "spot time". The total time t_view necessary to collect enough photons for one view is generally much longer than Δt. Therefore many different spots on the anode have to be visited while collecting data for one view. With prior art systems this is mostly realized by a rotating anode disk. Based on the foregoing relationship, it is apparent that in order to maintain the temperature at the anode surface constant, the spot time needs to be reduced if the power density is increased. For example, a doubling of power density requires a reduction of the spot time at the focal point by a factor of 4. In a more general fashion, increasing the power density by a factor of N requires reducing the spot time by a factor of N*N. Therefore, with, for example, the doubling of the power density (this is, increasing from P to 2*P) the spot time needs to be reduced to a quarter of the spot time Δt appearing in the above relationship as the spot time of a single visit with power density P. With the disclosed methodology this is realized by visiting each focus position multiple times during the acquisition of one view, and the spot time of each of those multiple visits would be a quarter of the former spot time Δt appearing in the above relationship as the spot time of a single visit with power density P. The time between two successive visits to the same focus position is then used to visit each of the other focus positions.

Figure 2A:
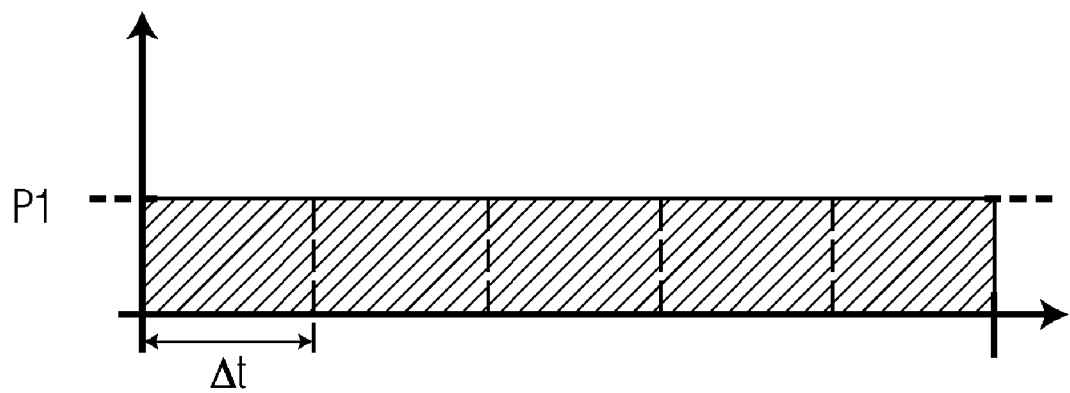
FIG. 2a is a plot of power densities relative to time for a conventional CT system implementation.

With reference to FIG. 2a, a plot of power density for focal positions relative to time in a conventional CT system is provided. In the plot of FIG. 2a, one focus is visited for the full time needed to collect enough photons for one view angle of the gantry (t_view), with power density P1 in the focal spot. This is done in such a way that the associated spot time is Δt, such that the temperature rise according to the above relationship is tolerable. In the given illustrative example, t_view is five times Δt.

Figure 2B:
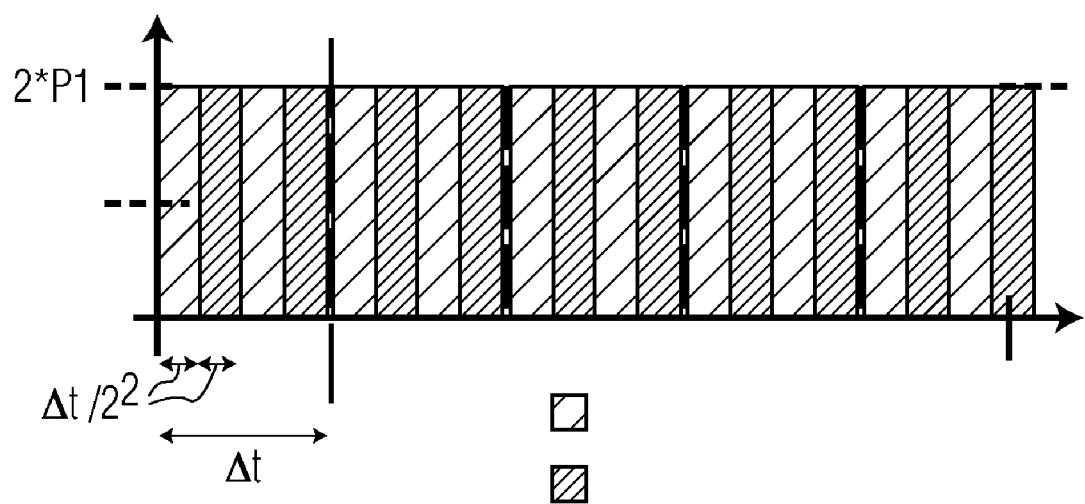
FIG. 2b is an exemplary plot of power densities relative to time according to a system implementation of the present disclosure.

In the plot of FIG. 2b, a series of two (2) focus positions along the Z-axis of the CT system is illustrated, and the power density is raised to 2*P1. According to the present invention, this can be realized without overheating the anode by decreasing the spot time for each focal spot to Δt*0.25 and by visiting each focal position twice during the time span Δt. The two focus positions depicted in FIG. 2b are merely illustrative and the CT system of the present disclosure may be employed with a different number of focus positions. Similarly, the plot of FIG. 2b is illustrative of an implementation of the present disclosure wherein the power density is doubled. However, the present disclosure is susceptible to wide ranging applications, including applications wherein the power density is increased to a greater or lesser degree than is illustrated in FIG. 2b, as will be readily apparent to persons skilled in the art. Of note, however, in selecting the number of focus positions employed, care should be exercised to ensure that the time interval between visits to a given focus position is not too short which could risk undesirable heat issues at the associated focal position on the anode surface.

The disclosed CT system and associated data acquisition methodology are particularly advantageous in that the photons required for a given projection can be produced in several different time slots, i.e., based on the repeated activation for a given view angle. As a result, the spot time may be decreased and the effective track velocity of the electron beam on the anode of the x-ray tube may be increased, thereby allowing the x-ray tube to be operated at higher peak power density without the attendant risks to the anode and overall x-ray tube operation. The disclosed CT systems advantageously exploit the "lateral" motion of the focus to increase the track velocity of the focus on the anode of the x-ray tube, thereby enabling higher power densities to be employed. Thus, unlike conventional CT systems that generate the requisite photons for each view angle in a single block of time, the disclosed CT system segregates/divides such photon generation into multiple time slots.

Figure 3:
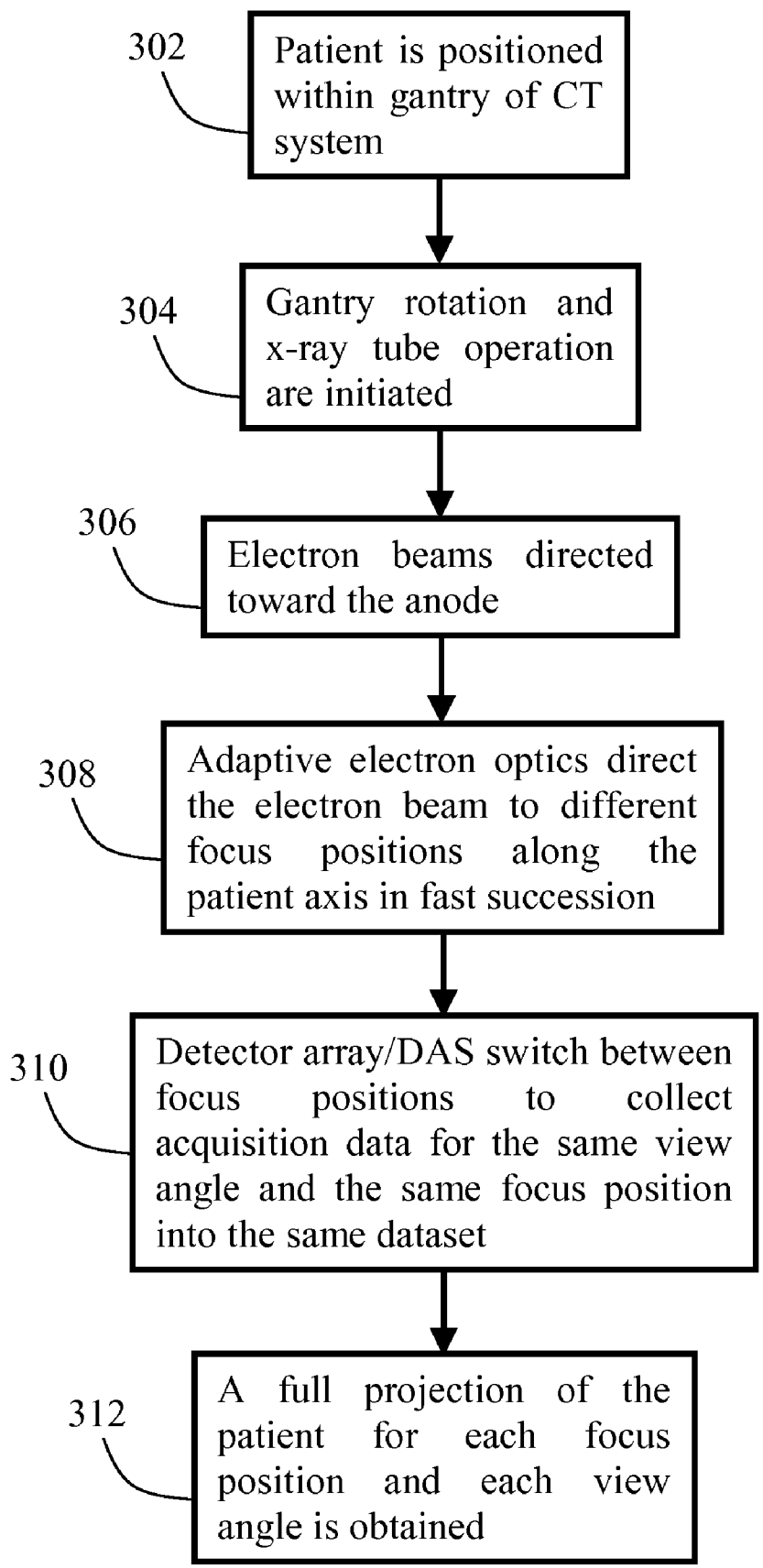
FIG. 3 is a flow chart of data acquisition and processing steps according to the present disclosure.

Reference is now made to FIG. 3 which provides a flow chart for operation of an exemplary CT system and data acquisition method according to the present disclosure. A patient is positioned 302 within the gantry of the CT system in substantial alignment with the z-axis thereof and rotation of the gantry is commenced 304. Electron beams are directed 306 toward the anode. In embodiments that include a single cathode and single anode (as described herein), electron beams are directed toward the anode and adaptive electron optics positioned therebetween function to move/scan the electron beam along the anode to a series of focal positions 308. In an alternative implementation of the disclosed CT system/technique, fast switching is performed between focus positions to collect the requisite detector array readings. In yet another alternative implementation, fast switching between focus positions is performed by switching between multiple cathodes. At step 310, the detector array and associated DAS switch between the different focus positions during data acquisition for one view angle so as to collect all acquisition data belonging to the same projection into the same data set. Based on such data acquisition, a full projection of the patient for each focus position and each view angle of the gantry is obtained 312.

The disclosed CT systems and data acquisition methods deliver higher time resolution (facilitating high quality images for moving objects, e.g., the heart) and/or higher spatial resolution (facilitating imaging of small structures/details, e.g., blood vessel properties). The benefits of the disclosed CT systems and data acquisition methods have wide ranging applicability, including, inter alia, medical imaging applications that require high temporal and/or spatial resolution, e.g., cardiac applications of computed tomography.

While the present disclosure has been described in terms of various specific embodiments, those skilled in the art will recognize that the disclosed invention can be practiced with various modifications, enhancements and/or variations without departing from the spirit or scope of the present disclosure. The present disclosure expressly encompasses within its scope such modifications, enhancements and/or variations as would be readily apparent to persons skilled in the art from the description provided herein.

The invention claimed is:

1. A computed tomography system, comprising:
   a rotatable gantry;
   at least one cathode mounted with respect to said gantry, said at least one cathode adapted to generate an electron beam;
   at least one anode defining an anode surface mounted with respect to said gantry;
   at least one detector array mounted with respect to said gantry; and
   adaptive electron optics positioned between said at least one cathode and said at least one anode;
      wherein said adaptive electron optics are adapted to move an electron beam generated by said at least one cathode to multiple focus positions along said anode surface of said at least one anode at each view angle of the computed tomography system.

2. A computed tomography system according to claim 1, wherein said at least one anode is an elongated cylindrical rotating anode.

3. A computed tomography system according to claim 1, wherein said at least one anode is an elongated helical anode.

4. A computed tomography system according to claim 1, wherein said at least one anode is selected from the group consisting of a saddle anode, stacked anode disks, and a collection of distinct anodes along a z-axis of the system.

5. A computed tomography system according to claim 1, further comprising a controller that controls operation of the gantry, the at least one cathode and the adaptive electron optics.

6. A computed tomography system according to claim 1, wherein said adaptive electron optics are adapted to move the electron beam along the anode surface to a plurality of focus positions.

7. A computed tomography system according to claim 6, wherein said adaptive electron optics are further adapted to move the electron beam to each of the plurality of focus positions multiple times.

8. A computed tomography system according to claim 1, wherein said at least one detector array is part of a data acquisition system (DAS).

9. A computed tomography system according to claim 8, wherein the DAS is adapted to switch between different focus positions for one view angle so as to collect data belonging to the same projection into a single data set.

10. A computed tomography system according to claim 1, wherein said adaptive electron optics are effective in moving the electron beam along the at least one anode surface to increase the power density without negatively impacting the operation of the anode.

11. A computed tomography system according to claim 1, wherein said detector array functions as part of a data acquisition system (DAS) that is effective to generate a full projection at each focus position and each view angle through activation of each focus position multiple times for each view angle of the gantry.

12. A computed tomography system, comprising:
  a rotatable gantry;
  at least one cathode mounted with respect to said gantry, said at least one cathode adapted to generate an electron beam;
  at least one anode defining an anode surface mounted with respect to said gantry;
  at least one detector array mounted with respect to said gantry; and
  adaptive electron optics positioned between said at least one cathode and said at least one anode;
    wherein said adaptive electron optics are adapted to effect switching at predetermined intervals, said switching being effective to direct the electron beam to different positions along the at least one anode surface.

13. A computed tomography system according to claim 12, wherein the at least one anode surface includes a plurality of anode elements.

14. A computed tomography system according to claim 12, wherein the predetermined intervals are short in duration.

15. A method for data acquisition in a computed tomography system, comprising:
  providing a computed tomography (CT) system that includes at least one cathode, at least one anode, and adaptive electron optics positioned therebetween;
  directing an electron beam from said at least one cathode toward said at least one anode, wherein said adaptive electron optics function to move said electron beam to a plurality of focus positions along the surface of said anode; and
  collecting data for each focus position at one view angle through multiple activations of the focus positions on the anode.

16. A method according to claim 15, wherein said at least one cathode, said at least one anode, and said adaptive electron optics are mounted with respect to a rotatable gantry.

17. A method according to claim 16, further comprising collecting data with a detector array mounted with respect to said gantry.

18. A method according to claim 17, wherein said detector array is part of a data acquisition system (DAS) that is adapted to switch between the different focus positions during data acquisition for one view angle and to collect acquisition data belonging to the same projection into a single data set.

19. A method according to claim 17, wherein said detector array is a multi-slice cone-beam detector or a photon counting detector.

20. A method according to claim 15, wherein said adaptive electron optics are adapted to move said electron beam from a first focal position to a second focal position after a predetermined time interval.

21. A method according to claim 20, wherein said predetermined time interval is of equal duration for each focal position defined on said anode.

22. An x-ray tube for use in a computer tomography system, the x-ray tube comprising:
  one or more cathodes adapted to generate an electron beam; and
  one or more anodes defining an anode surface,
    wherein adaptive electron optics are positioned between at least one cathode and at least one anode for moving an electron beam generated by the at least one cathode to multiple focus positions along the anode surface at each view angle of the computed tomography system.

23. The x-ray tube of claim 22, wherein the adaptive electron optics are effective in moving the electron beam along the at least one anode surface to increase the power density without negatively impacting the operation of the at least one anode.

* * * * *